United States Patent [19]
Cimini et al.

[11] Patent Number: 5,797,921
[45] Date of Patent: Aug. 25, 1998

[54] DISPOSABLE CIRCUMCISION APPARATUS AND METHOD OF USE

[75] Inventors: Catherine M. Cimini, Somerset, N.J.; James A. Mawhirt, Brooklyn, N.Y.

[73] Assignee: International Technidyne Corporation, Edison, N.J.

[21] Appl. No.: 819,426

[22] Filed: Mar. 17, 1997

[51] Int. Cl.$^6$ ............................................. A61B 17/32
[52] U.S. Cl. ................................. 606/118; 606/167
[58] Field of Search ............................ 606/1, 118, 135, 606/167, 174, 180, 205–211

[56] References Cited

U.S. PATENT DOCUMENTS

| | | | |
|---|---|---|---|
| 1,417,142 | 5/1922 | Couch | 606/118 |
| 2,376,893 | 5/1945 | Baker | 606/118 |
| 3,111,124 | 11/1963 | Rodbard | 606/118 |
| 3,612,057 | 10/1971 | Freedman | 606/118 |
| 3,783,875 | 1/1974 | Winshel . | |
| 3,789,848 | 2/1974 | Honjyo . | |
| 4,491,136 | 1/1985 | LeVeen . | |
| 5,163,943 | 11/1992 | Mohiuddin et al. . | |
| 5,269,788 | 12/1993 | Nelson, III . | |
| 5,329,934 | 7/1994 | Bowman . | |
| 5,344,396 | 9/1994 | Clark, Jr. . | |
| 5,439,466 | 8/1995 | Kilejian . | |

*Primary Examiner*—Glenn K. Dawson
*Attorney, Agent, or Firm*—Plevy & Associates

[57] ABSTRACT

A method for circumcising a penis having a foreskin encircling the glans penis using an apparatus having a cap, a guide clamp, and a blade holder mechanism. The cap defines an interior space and has an outer surface. The glans penis of the penis is placed in the interior space defined by the cap. The foreskin of the penis is positioned around an outer surface of the cap. The clamp is positioned over the foreskin such that a portion of the foreskin is interposed between the clamp and specific features on the outer surface of the cap. The guide clamp is secured in a position over the foreskin of the penis crushing the skin to prevent bleeding. The blade holder mechanism is placed on the guide clamp and rotated around the guide clamp so that a blade carried by the blade holder mechanism cuts the foreskin. The blade is mounted on a flexible finger within the blade holder and as such is exposed for cutting only during use. At all other times the blade is safely contained within the blade holder body.

17 Claims, 6 Drawing Sheets

DISPOSABLE CIRCUMCISION APPARATUS AND METHOD OF USE

FIELD OF THE INVENTION

The invention relates to a circumcision apparatus and more particularly a simple, lightweight disposable circumcision apparatus.

BACKGROUND OF THE INVENTION

The circumcision of male infants is practiced for both health and religious reasons. Circumcision is the removal of a portion of the foreskin from the glans penis. Circumcision has typically been done with large cumbersome metal implements that are used repeatedly and hopefully sterilized before each use. One or more implements are attached to the infant's penis and hang down with the entire weight being borne by the infant's body.

A purported disposable circumcision device is disclosed in U.S. Pat. No. 4,491,136. The device has a cylindrical tube member including a separable inner ring having an annular groove. The cylindrical tube, including the inner ring, is fitted between the foreskin and glans penis. A second member surrounds the foreskin and the cylindrical tube member. The second member has a compression member and an outer ring. The outer ring and the inner ring are aligned with the foreskin interposed. The compression member is removed from the outer ring to cause the outer ring to shrink to compress the foreskin of the penis between the rings.

The foreskin is then surgically excised by an undisclosed method. It is presumed that the doctor or person performing the circumcision with the disposable circumcision device of the '136 patent uses a scalpel to cut the foreskin. The position, depth, and other factors of the cut depend on the person performing the circumcision.

It would be desirable to have a disposable circumcision apparatus that is light and easy to use, as it guides and contains the cut to give predictable results, and safely stores the blade before and after use.

SUMMARY OF THE INVENTION

This present invention is directed to a method of and apparatus for circumcising a penis having a foreskin encircling the glans penis. The apparatus has a cap defining an interior space and having an outer surface, a guide clamp, and a blade holder mechanism. The glans penis of the penis is placed in the interior space defined by the cap. The foreskin of the penis is positioned around an outer surface of the cap. The guide clamp is securely positioned over the foreskin such that a portion of the foreskin is interposed between the guide clamp and the outer surface of the cap. The blade holder mechanism is placed on the guide clamp and rotated around the guide clamp so that a blade carried and protected by the guided blade holder mechanism cuts the foreskin.

One object, feature, and advantage resides in the guide clamp having an inner edge for engaging and crushing the foreskin between the cap and the edge of the clamp. Another feature is the outside diameter of the clamp acts as a guide for the positioning and rotation of the blade holder and the blade.

Another object, feature, and advantage resides in the blade holder mechanism generally having a "C" shaped main section and a flexible finger, the main "C" section having a channel through which the flexible finger carrying the blade can pass, and subsequently return for safe storage. Since the blade is attached to the "flexible finger," the blade is exposed during use and is withdrawn within the main "C" section for safe storage use.

Further objects, features, and advantages of the present invention will become more apparent to those skilled in the art as the nature of the invention is better understood from the accompanying drawings and detailed descriptions.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE PREFERRED EMBODIMENT

Figure 1:
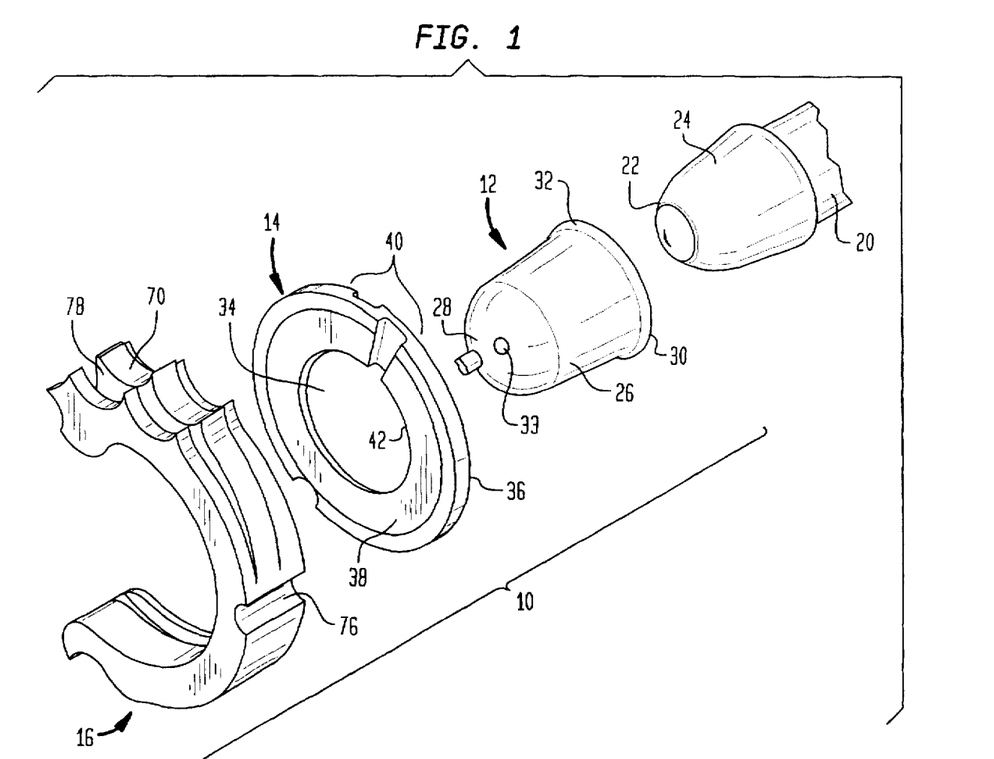
FIG. 1 is a perspective of components of the apparatus according to the invention.

Referring now to the drawings, wherein like numerals indicate like elements, there is shown in FIG. 1 a perspective view of a circumcision apparatus which has been identified by the numeral 10.

Figure 5:
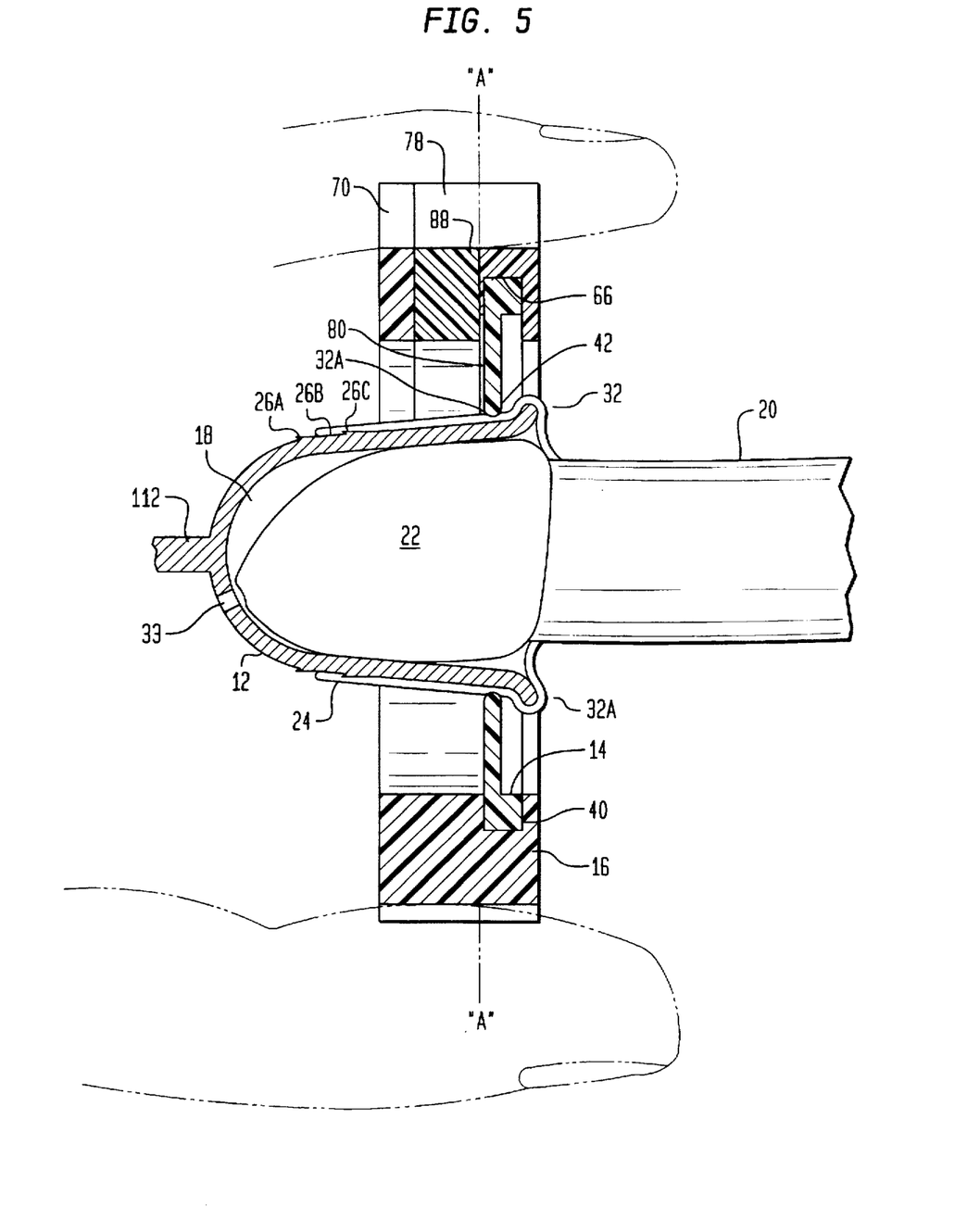
FIG. 5 is a sectional view of the apparatus assembled on and around the penis. The user's fingers are shown in phantom.

Referring to FIG. 1, the circumcision apparatus 10 has a cap 12, a guide clamp 14, and a blade holder mechanism 16. The cap 12 is generally cylindrical and defines an interior space 18, as seen in FIG. 5, adapted to receive the glans penis 22 of a penis 20, with the foreskin or prepuce 24 positioned and secured on an outer surface 26 of the cap 12. The outer surface 26 contains several annular sharp or crisp features, 26A, 26B, and 26C which will help the foreskin remain taught for the cutting operation. The foreskin will be gripped as it is pulled and stretched over the outer cap surface 26. The cap 12, in a preferred embodiment, is generally a bell shape and tapers from a closed protective vented head end 28 to an open mouth end 30. The open mouth end 30 has a lip 32 which projects outward. The closed end has a vent hole 33, as best seen in FIG. 5, to facilitate removal from a tight fitting moist glans penis.

Figure 2:
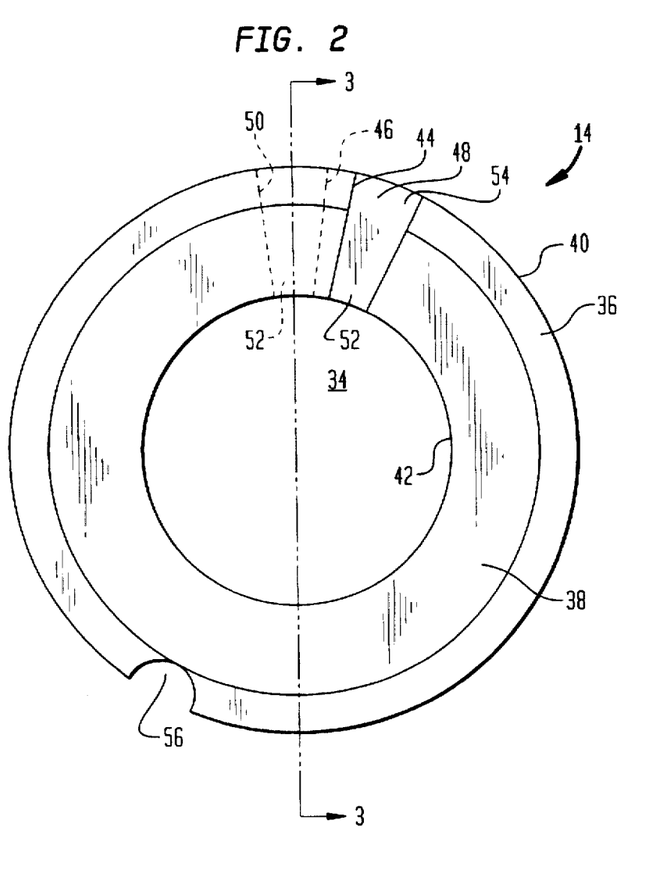
FIG. 2 is a front view of a guide clamp.
Figure 3:
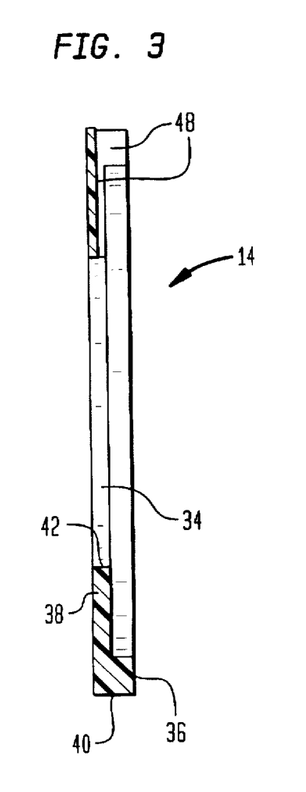
FIG. 3 is a sectional view of the guide clamp taken along line 3—3 of FIG. 2.

The guide clamp 14 is generally annular in shape and defines an opening 34, as seen in FIGS. 2 and 3. The guide clamp 14 has an outer annular support ring portion 36 and an inner annular, thin, ring portion 38. The inner annular ring 38 and the outer annular support ring 36 are formed integrally as one part. The guide clamp 14 has a cut in the annular shape which extends from an outer edge 40 to the opening 34, located at an inner edge 42. The cut defines a pair of mating edges 44 and 46; one of the mating edges 46 is shown in hidden line in FIG. 2.

The outer annular support ring 36 has a pair of securing tabs 48 located at the mating edges 44 and 46. The securing tabs 48 overlap to secure the clamp 14 as described below. Each of the tabs 48 is approximately half the thickness of the remainder of the outer annular support ring 36, as best seen in FIG. 3. The origin of the securing tab 48 portion on the mating edge 44 side is shown by a hidden line 50 in FIG. 2. The tabs 48 each have an inside surface 52 with a plurality of ratchet type teeth 54 which engage to limit movement of mating edges 46 relative to each other and secure the crimping action of the inner edge 42. The outer annular support ring 36 has a flex notch 56 to allow the clamp 14 to be adjusted in size or cinched in order for the clamp 14 to crush the foreskin 24 of the penis 20, as described below.

The inner edge 42 of the inner annular thin ring portion 38 which surrounds the opening 34 is a tapered crisp edge 42. The tapered crisp edge 42 is used to crush the foreskin 24 as described below. The inner tapered crisp edge 42 will overlap when the guide clamp 14 is in a closed crushing position. The outer edge 40 of the guide clamp 14 is also referred to as a guide edge and is received by the blade holder mechanism 16.

Figure 4:
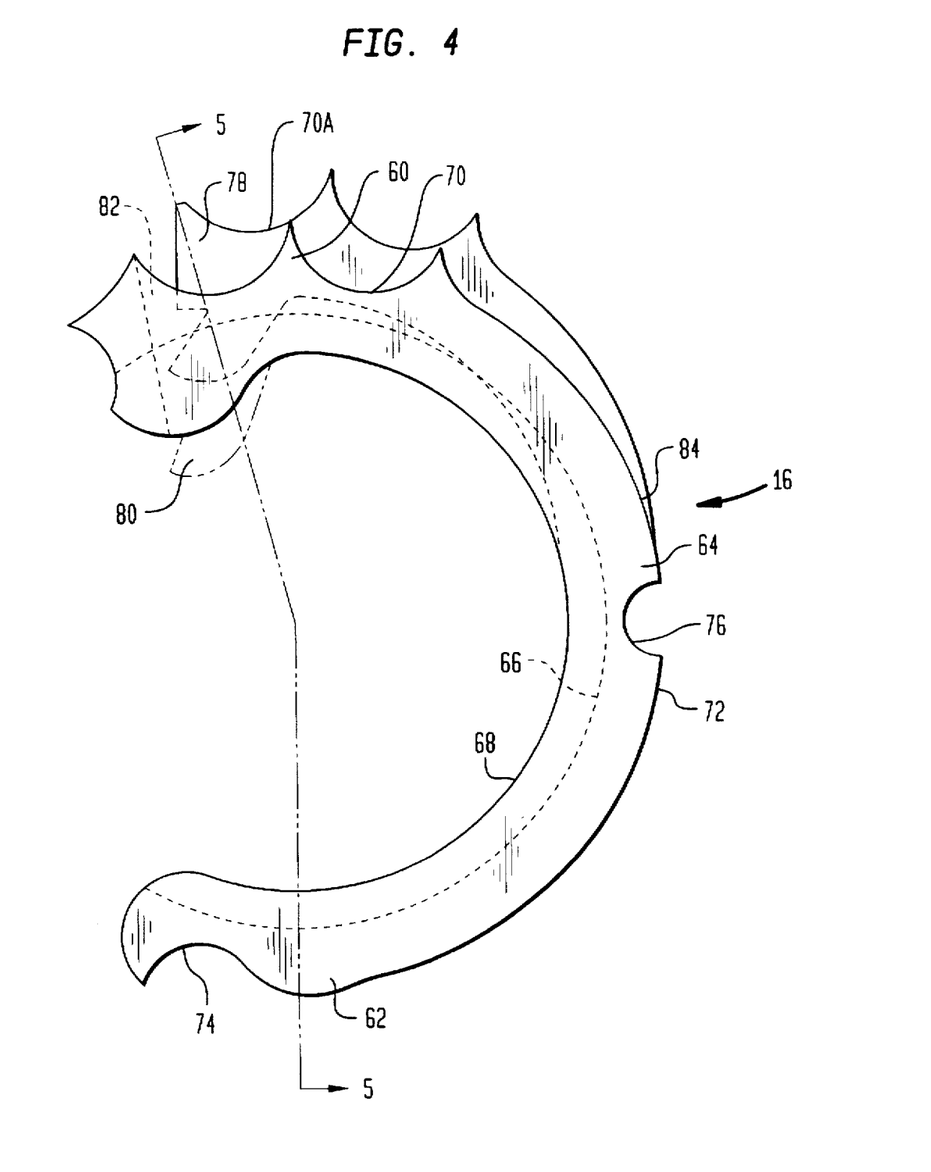
FIG. 4 is a front view of a blade holder mechanism. A portion of the flexible blade finger with a blade of the blade guide mechanism in a retracted released position is shown in hidden line. The blade of the blade guide mechanism is shown in phantom in a depressed cutting position.
Figure 8:
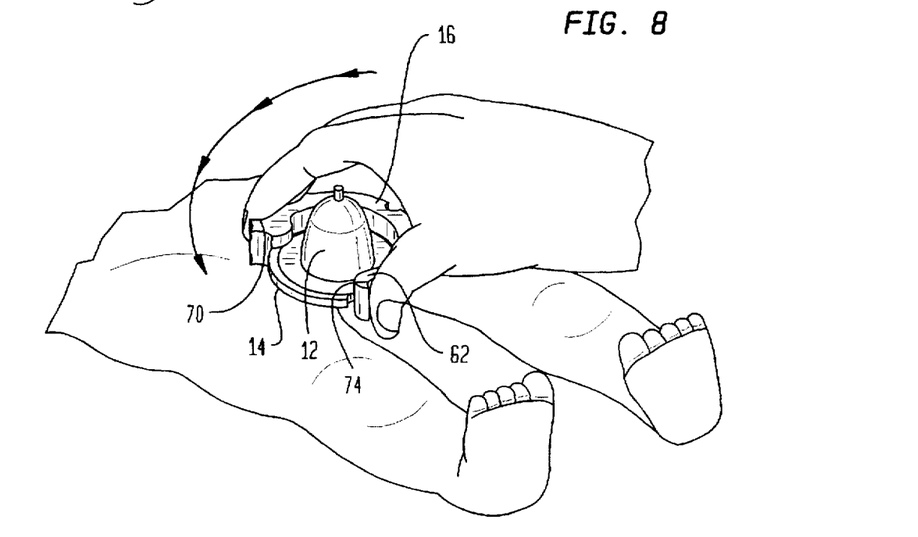
FIG. 8 is a perspective view of the circumcision apparatus in use.

Referring to FIG. 4, the blade holder mechanism 16 is generally "C" shaped and has a pair of legs 60 and 62 and a base section 64 interposed between the legs 60 and 62. The blade holder mechanism 16 has a clamp glide slot 66, shown in hidden line, which opens onto an inner edge 68 of the blade holder mechanism 16. The blade holder mechanism 16 also has a pair of depressions, contours, or concave surfaces 70 on an outer edge 72 of one leg 60 adapted to receive a user's index and middle fingers. The other leg 62 has a single depression, contour, or concave surface 74 on the outer edge 72 adapted to receive the user's thumb, as seen in FIGS. 5 and 8. Similar to the guide clamp 14, the blade holder mechanism 16 has a flex notch 76 on the blade holder mechanism's 16 outer edge 72 on the base 64. The blade holder mechanism 16 can be used in the left or right hand.

The blade holder mechanism 16 has a flexible finger 78 which carries a secured blade 80, shown in hidden line and phantom. The flexible finger 78 is located in and passes through a slot or channel 82, shown in hidden line, in one of the legs 60 of the blade holder mechanism 16. A portion of the leg 66 projects inward in order to cover the blade 80 which is in a concealed position when the finger 78 is in a retracted released position. The flexible finger 78 is formed integrally with the remainder of the blade holder mechanism 16 and joined by a living hinge generally designated at 84. The flexible finger 78 has a pair of depressions or concave surfaces 70 which align with the depressions 70 on the leg 60 when then finger 78 is in a depressed engaged position, as shown in phantom.

The interrelation of the cap 12, the guide clamp 14, and the blade holder mechanism 16 with the foreskin 24 of the penis 20 to be cut is shown in FIG. 5. The guide clamp slot 66 of the blade holder mechanism 16, which receives the guide clamp 14, is offset from a center line "A" of the blade holder mechanism 16. The flexible finger 78, which is located on the other side of the center line "A" of the blade guide mechanism, has the blade 80 mounted on an edge 88 which is located in proximity to the center line "A" and the clamp guide slot 66.

The guide clamp 14 is in a closed crushing position with the outer edge 40 located in the clamp guide slot 66. The inner tapered crisp edge 42 engages the foreskin 24 of the penis 20 which is located on the outer surface 26 of the cap 12 and is precisely and firmly positioned by the nesting of the crisp edge 42 into a receiving slot, a circumferential recess 32A, of the cap 12 and kept taught by the crisp annular features 26A, B, and C on the outer diameter of the cap 12 and the outer most corners are sharpened or serrated to clear the connecting membrane 24A. The foreskin 24 extends from the glans penis 22 around the lip 32 of the cap 12 and lies on the outer surface 26 of the cap 12. The guide clamp 14 is cinched such that the foreskin 24 is crushed between the recess 32A of the cap 12 and the inner tapered crisp edge 42 of the guide clamp 14. This crimping action is required to crush the captured foreskin and prevent bleeding after the circumcision is completed. The glans penis 22 is located in the interior space 18 defined by the cap 12.

One of the depressions 70 on the leg 60 of the blade guide mechanism 16 is shown. The user's fingers are shown in phantom. The blade is shown engaging the foreskin 24 of the penis 20. The circumferential recess 32A of the open mouth end 30 captures and guides the blade 80 during use.

Figures 6, 6A, 6B:
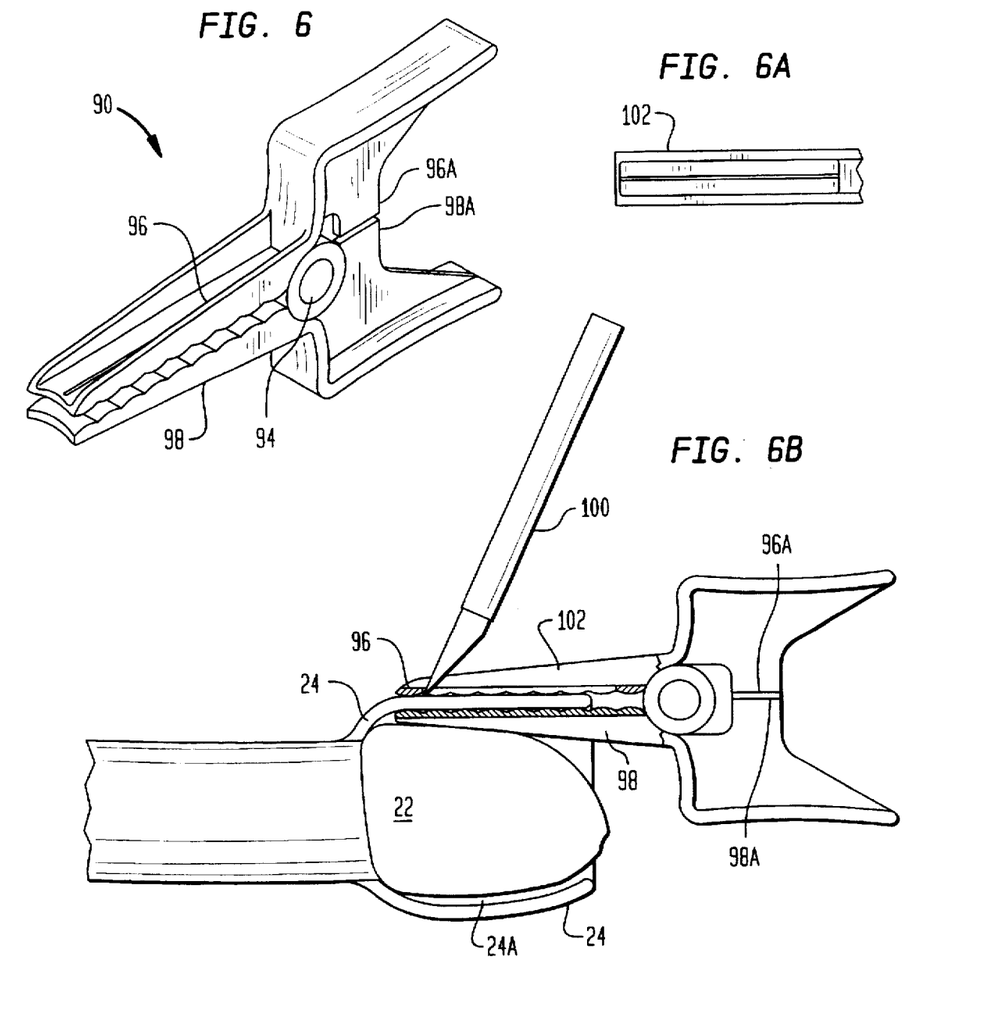
FIG. 6 is a perspective view of a safety prep clamp cutter.
FIG. 6A is a top view of one of the plates of the safety cutter.
FIG. 6B is a sectional view of the safety cutter with the penis.
Figure 6C:
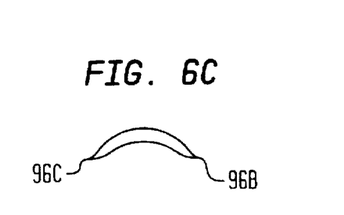
FIGS. 6C and 6D are views of the jaws of the safety prep clamp cutter.
Figure 6D:
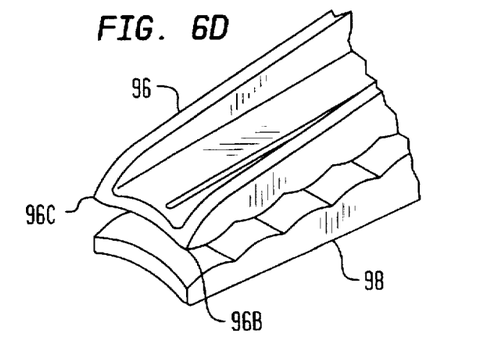

The circumcision apparatus 10, in a preferred embodiment, has a safety cutter guide 90, as seen in FIG. 6. The safety cutter guide 90 is a scissor type clamp with a hinge portion 94 located between a pair of curved plate-like jaws 96 and 98. The upper jaw 96 has a guide groove 102, as seen in FIG. 6A, adapted to receive a blade 100. The guide groove 102 does not extend through the lower jaw 98, therefore the blade 100 can only cut items located between the two jaws 96 and 98. The safety cutter guide 90 is used to clear the membrane connecting the glans penis 22 and the foreskin 24. The sharpened edges 96B and C shown in FIGS. 6C and 6D are positioned between the foreskin 24 and the glans penis 22 engaging the membrane 24A. The SC Guide 90 is rotated after insertion, tearing the membrane 24A as the guide 90 is rotated 360°. The cutting or tearing edges are shaped so that the inner corner contacts the glans penis smoothly without possible cuts or abrasions. The safety cutter guide 90 is also used to cut the foreskin 24 axially as required at the beginning of the procedure to facilitate placement and stretching of the foreskin 24 over the cap 12 gripping by annular edges 24A, B, and C and full insertion of the glans penis into the cap 12.

Each of the jaws 96 and 98 have on the other side of the hinge 94 a plurality of ratchet teeth 96A and 98A. The teeth, similar to that in the guide clamp 14, are designed to engage to limit the movement of the jaws 96 and 98 during use.

Figure 7:
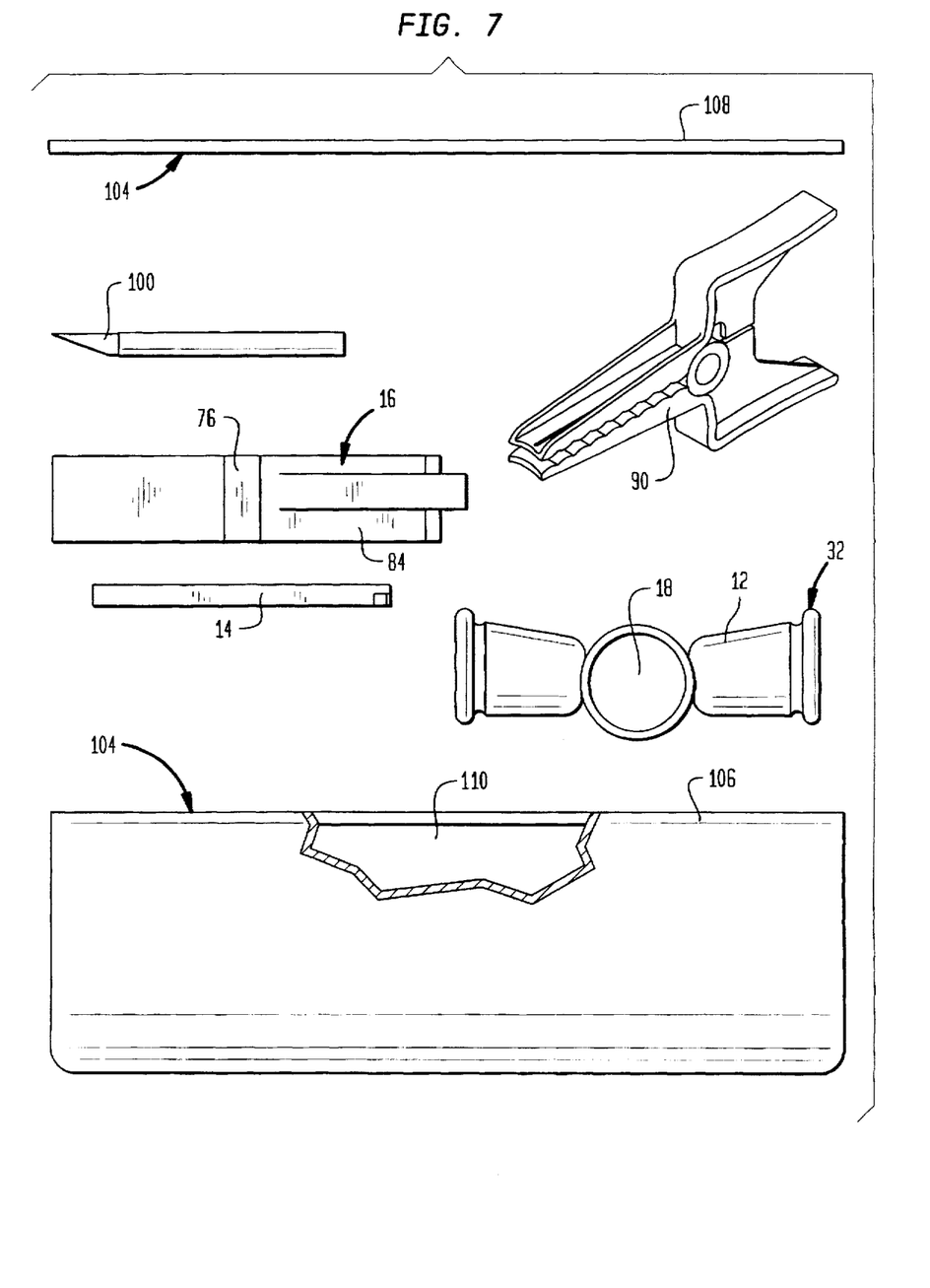
FIG. 7 is an exploded side view of the clamp, cap, blade holder mechanism, and safety cutter in a container to maintain sterility prior to use, having a vessel and a lid.

The circumcision apparatus 10, in a preferred embodiment, has a container 104 including a vessel 106 and a lid 108. The vessel 106 has an interior space 110 which receives the cap 12, the guide clamp 14, the blade holder mechanism 16, and the safety cutter 90.

In a preferred embodiment, the circumcision apparatus 10 has multiple caps 12, of all different sizes. The caps 12 can be connected to each other, by each cap having a shaft 112, as seen in FIG. 5, extending from the closed head end 28 to a ringlet. Likewise, in a preferred embodiment, the cap 12, the clamp 14, the safety cutter guide 90, and the blade guide mechanism 16, with the exception of the secured blade 80, are made of plastic.

In operation

When a doctor, religious leader, or other person is ready to perform the circumcision, the location where the circumcision is to occur is sterilized and the male infant is positioned for the operation. The container 104 of the circumcision apparatus 10 is opened by removing the lid 108 from the vessel 106 exposing the sterilized components, as seen in FIG. 8.

Referring to FIGS. 1 and 5, the user selects the proper size cap 12 for the penis 20. The cap 12 is placed on the penis 20 such that the glans penis 22 is located in the interior space 18 of the cap 12. The foreskin 24 of the penis 20 is positioned around the outer surface 26 of the cap 12.

Referring to FIG. 6, if the foreskin 24 of the penis 20 encircles the glans penis 22 such that it is difficult or impossible to place the cap 12 between the foreskin 24 and the glans penis 22, the foreskin 24 can be axially crushed and axially cut first using the safety cutter guide 90 and the blade 100.

The lower jaw 98 of the safety cutter guide 90 is inserted between the glans penis 22 and the foreskin 24, such that the foreskin is stretched over the lower jaw 98 toward the hinge 94 of the safety cutter guide 90. The forward tip of the lower jaw 98 extends into and between the glans penis and the foreskin to just beyond the circumcision zone. To facilitate full insertion the membrane 24A must first be cleared. The lower jaw 98 is rotated 360° around and the sharpened edges 96B and 96C cut and clear the connecting membrane 24A. The membrane cutting is done with the ratchets 96A and 98A disengaged which will permit rotation of the separated jaws 96 and 98.

With the notched extensions of the jaws 96 and 98 gripped, the jaws are compressed. The plurality of ratchet teeth 96A and 98A of the jaws 96 and 98 hold the jaws 96 and 98 in position. When the cinching compression and crushing are complete, the foreskin 24 is cut using the knife 100 which is guided by the guide slot 102. The blade 100 moves axially towards the edge of the foreskin 24, creating an axial cut in the foreskin 24. The glans penis is protected from the blade by the solid lower jaw 98. After the axial cut is completed and the foreskin is sized to fit over the cap 12, the safety cutter guide 90 can be removed by disengaging the mating ratchet type features 96A and 96B.

Referring to FIG. 5, after the cap 12 is positioned on the glans penis 22, the guide clamp 14 is positioned over the foreskin 24 such that the foreskin 24 is interposed between the guide clamp 14 and the outer surface 26 of the cap 12. The guide clamp 14 is cinched by pushing the mating edges 44 and 46 together and engaging them into groove 32A. The teeth 54 on the inner surfaces 52 of the securing tabs 48, as seen in FIG. 2, the engage to hold the guide clamp 14 in the closed crushing position.

The blade holder mechanism 16 is placed over the guide clamp 14, such that the outer guide edge 40 of the guide clamp 14 is located in the clamp glide slot 66 of the blade holder mechanism 16. The user places his/her hand such that her ring finger and little finger are located on the depressions or concave surfaces 70 on the flexible finger 78, as seen in FIG. 8. The thumb is positioned on the depression or concave surface 72 on the leg 62 of the blade guide member 16, as seen in FIG. 8. The flexible finger 78 is depressed so that the blade 80 moves from the concealed position when the flexible finger 78 moves from the retracted released position to the depressed engaged position. With the blade 80 engaging the foreskin 24, the user rotates the blade holder mechanism 16 around the guide clamp 14, cutting the foreskin 24. The blade 80 engages and follows the circumferential recess 32A as long as the grip is maintained.

Upon completion of the cut, the blade holder mechanism 16 is removed by disengaging the mating edges 44 and 46.

The blade is safely retracted within the blade holder 16. The guide clamp 14, which was located just inward of the cut and crushed the foreskin 24 to minimize bleeding, is removed. The cap 12 is then removed. The circumcision apparatus 10 including the safety cutter guide 90 and the blade 100, and the removed foreskin 24 are both disposed of properly.

The present invention may be embodied in other specific forms without departing from the spirit or essential attributes therefore and, accordingly, references should be made to appended claims, rather than to the foregoing specification, as indicating the scope of the invention. For example, it is recognized that it may be desirable to have a latching mechanism to ensure the ratchet type teeth 54 of the two inside surfaces 52 of the clamp guide 14 stay engaged and a releasing mechanism to release the latching mechanism. It is also recognized that it may be desirable to angle the blade such that it engages the cap close to the clamp guide 14.

We claim:

1. An apparatus for circumcising a penis having a glans penis and a foreskin, the apparatus comprising:
    a cap defining an interior space and having an outer surface, the interior space adapted to receive the glans penis of the penis, the outer surface adapted to receive the foreskin;
    a clamp having an opening for encircling a portion of the cap and holding the foreskin in engagement with the outer surface of the cap; and
    a blade guide mechanism having a guide slot on an interior edge adapted to receive a portion of the clamp for guiding the blade guide mechanism around the cap and a blade adapted to engage and cut the foreskin.

2. An apparatus for circumcising a penis having a glans penis and a foreskin as in claim 1 wherein the clamp has an edge for engaging the foreskin, therein crushing the foreskin between the cap and the edge of the clamp.

3. An apparatus for circumcising a penis having a glans penis and a foreskin as in claim 1 wherein the clamp further comprises a guide edge to be received by the guide slot of the blade guide mechanism for guiding the blade guide mechanism around the clamp.

4. An apparatus for circumcising a penis having a glans penis and a foreskin as in claim 3 wherein the clamp has an edge for engaging the foreskin, therein crushing the foreskin between the cap and the edge of the clamp.

5. An apparatus for circumcising a penis having a glans penis and a foreskin as in claim 4 wherein the blade guide mechanism generally has a "C" shaped main section and a flexible finger, the main "C" section having a channel through which the flexible finger can pass, the flexible finger carrying the blade and formed integrally with the main "C" section and connected by a flexible hinge, the flexible finger adapted to move between a retracted released position and a depressed engaged position.

6. An apparatus for circumcising a penis having a glans penis and a foreskin as in claim 5 wherein the main "C" section of the blade guide mechanism has a flex notch on an outer edge.

7. An apparatus for circumcising a penis having a glans penis and a foreskin as in claim 6 wherein the main "C" section of the blade guide mechanism has a concave surface adapted to receive the users' hand.

8. A kit for circumcising a penis having a glans penis and a foreskin, the kit comprising:
    at least one cap defining an interior space and having an outer surface, the interior space adapted to receive the glans penis of the penis, the outer surface adapted to receive the foreskin;

a clamp having an opening for encircling a portion of the cap and holding the foreskin in engagement with the outer surface of the cap;

a blade guide mechanism generally having a "C" shape and having a guide slot adapted to receive a portion of the clamp for guiding the blade guide mechanism around the cap and a blade adapted to engage and cut the foreskin; and an axial cutter having a blade and a clamping device having a pair of jaws, one of the jaws having a guide groove and the other jaw adapted for protecting the glans penis.

9. A kit for circumcising a penis having a glans penis and a foreskin as in claim 8, the kit further comprising:

a container having a space adapted to receive at least one cap, a clamp, a blade guide mechanism, a safety guide cutter, and a blade; and a lid adapted to be received by the container for sealing the space.

10. A kit for circumcising a penis having a glans penis and a foreskin as in claim 9, the kit further comprising a plurality of caps, at least one cap being of a different size.

11. A kit for circumcising a penis having a glans penis and a foreskin as in claim 8 wherein the clamp further comprises a guide edge to be received by the guide slot of the blade guide mechanism for guiding the blade guide mechanism around the clamp and an inner edge for engaging and crushing the foreskin between the cap and the edge of the clamp, and wherein the blade guide mechanism has a main "C" section and a flexible finger, the main "C" section having a slot through which the flexible finger can pass, the flexible finger carrying the blade and formed integrally with the "C" section and connected by a flexible hinge.

12. A kit for circumcising a penis having a glans penis and a foreskin as in claim 11 wherein the main "C" section of the blade guide mechanism has a flex notch on an outer edge.

13. A kit for circumcising a penis having a glans penis and a foreskin as in claim 12 wherein the main "C" section of the blade guide mechanism has a concave surface adapted to receive the users' hand.

14. A method of circumcising a penis having a foreskin encircling the glans penis, the method comprising the following steps:

providing a cap defining an interior space;

placing the glans penis of the penis in the interior space defined by the cap;

positioning the foreskin of the penis around an outer surface of the cap;

positioning a clamp over the foreskin such that a portion of the foreskin is interposed between the clamp and the outer surface of the cap;

securing the clamp in the position over the foreskin of the penis;

placing a blade guide mechanism on the clamp; and cutting the foreskin of the penis with a blade carried by the blade guide mechanism by flexing the blade guide mechanism to expose the blade from a concealed position to engage the foreskin and rotating the blade guide mechanism around the clamp and the foreskin.

15. A method of circumcising a penis having a foreskin encircling the glans penis as in claim 14, wherein securing the clamp in the position over the foreskin of the penis further comprises crushing the foreskin of the penis with a crisp edge of the clamp by cinching the clamp.

16. A method of circumcising a penis having a foreskin encircling the glans penis as in claim 15, further comprising the step of cutting the foreskin axially with a cutter having a blade and a receiving plate having a guide groove, the blade and receiving plate connected by a flexible band.

17. A method of circumcising a penis having a foreskin encircling the glans penis as in claim 14, further comprising the step of selecting a cap from a plurality of caps wherein the securing the clamp in the position over the foreskin of penis further comprises crushing the foreskin of the penis with a crisp edge of the clamp by cinching the clamp.

* * * * *